United States Patent [19]
Taylor

[11] 4,057,066
[45] Nov. 8, 1977

[54] CATHETER HOLDER FOR SECURING A URETHRAL CATHETER TO A PATIENT

[76] Inventor: Harry E. Taylor, 22 Taylor Drive, Bradford, Pa. 16701

[21] Appl. No.: 720,085

[22] Filed: Sept. 2, 1976

[51] Int. Cl.² .................................................. A61M 25/02
[52] U.S. Cl. .......................... 128/349 R; 128/DIG. 26; 248/205 A; 24/DIG. 11
[58] Field of Search .................................. 128/348–351, 128/133, DIG. 26; 24/18, 73 R, 73 SH, 73 VA, 243 CH, DIG. 11; 248/205 A

[56] References Cited
U.S. PATENT DOCUMENTS

| 2,486,593 | 11/1949 | Gardner | 248/205 A |
| 3,677,250 | 7/1972 | Thomas | 128/348 |
| 3,990,454 | 11/1976 | Schlesinger | 128/349 R |

OTHER PUBLICATIONS

Quinton et al., Trans. Amer. Soc. Art. Inter. Orgs., vol. VIII, Apr. 13, 1962, pp. 236-243.

*Primary Examiner*—Dalton L. Truluck
*Attorney, Agent, or Firm*—Smith, Harding, Earley & Follmer

[57] ABSTRACT

A catheter holder for securing a urethral catheter to a patient includes an anchoring strip with a pressure-sensitive adhesive layer on one side covered by a peel-off cover sheet. A cord passes through a pair of adjacent openings in the anchoring strip with the cord being tied to secure it to the anchoring strip. The anchoring strip in the area of the openings is reinforced by a reinforcing panel. The cord is looped around a peripheral groove in a connector between the catheter and a drain tube and tied to secure it in the peripheral groove against longitudinal movement.

2 Claims, 5 Drawing Figures

CATHETER HOLDER FOR SECURING A URETHRAL CATHETER TO A PATIENT

BACKGROUND OF THE INVENTION

The need for a satisfactory urethral catheter holding device has existed in hospitals for a long time.

Experimentation with different types of adhesive devices were unsatisfactory because they did not remain attached to the patient's leg or the catheter would slip out of the device.

Stretch rubber straps and VELCRO fastening devices which encircled the thigh were unsatisfactory because: (1) if they were tight enough to stay in position they had a constricting effect, interfering with venous return from the lower leg and (2) if they were too loose they would slip distally on the thigh thereby causing pull on the urethral catheter, resulting in patient discomfort.

A variety of ways are employed to secure a medical tube or the like to a patient as is shown in the following patents: U.S. Pat. Nos. 2,159,947; 2,727,512; 2,898,917; 3,430,300; 3,542,321; 3,677,250; 3,683,911; 3,826,254; 3,834,380; 3,900,026; and 3,918,446. A device for receiving such a tube and securing it to the patient's skin by an adhesive, for example a pressure-sensitive adhesive, is shown in U.S. Pat. Nos. 2,727,512; 2,898,917; 3,430,300; 3,542,321; 3,683,911; and 3,834,380. These devices fail to provide adequate security against longitudinal movement of the medical tube. U.S. Pat. Nos. 3,677,250 and 3,826,254 disclose typical prior art devices in which the medical tube is engaged by a tape or the like that is adhesively secured to the tube. These devices are difficult to secure to the medical tube. When the tape is secured directly to the medical tube, it can pinch the tube closed.

In the hospitals, a catheter may be inserted in a patient and may have its inner end positioned within the urinary bladder, kidney, ureter, biliary ducts, the thorax, or other body cavity.

It is desired to prevent the catheter from pulling out of the bladder, and it has been conventional to fasten the catheter to the leg of a patient by means of rubber bands. More recently, VELCRO attaching means have been used to attach the catheter to the leg of the patient.

These attaching devices have been somewhat less than satisfactory because they can slide up and down the leg of the patient, especially if the patient is walking.

The invention is highly advantageous over the prior art in that it provides complete security against unwanted longitudinal movement of a urethral catheter even with extensive movement of the patient. It is also advantageous in that it provides for attachment and removal of the urethral catheter or a drain tube without removal of the securing device. It also provides for a very simple and quick attachment and removal of the connector between the urethral catheter and drain tube.

BRIEF SUMMARY OF THE INVENTION

A catheter holder for securing a urethral catheter to a patient includes an anchoring strip with a pressure-sensitive adhesive layer on one side for securing the strip to a patient's skin. A cord is secured to the anchoring strip and looped around a peripheral groove in a connector between the catheter and a drain tube, and tied to secure it in said groove to prevent longitudinal movement of the connector and catheter. Advantageously, the anchoring strip has a pair of openings through which the cord passes and the cord is tied to secure it to the anchoring strip; and the strip has a reinforcing panel adjacent the openings.

This holder is constructed of an adhesive-backed fabric, a centrally placed reinforcement strip, and a piece of umbilical tape about 16 inches long.

There are two holes in the device in the area of the reinforcement strip. The umbilical tape is passed through one hole from the top side and back up through the second hole. The tape is then tied snugly between the two holes on the top side in such a manner that the tails are of equal length. The reinforcement strip prevents the umbilical tape from cutting through the device between the two holes.

The holder generally seems to be most satisfactory when it is placed on the antero-medial aspect of the thigh about midway between the perineum and the knee, with its long axis running parallel to the shaft of the femur. The exact location can best be ascertained when the catheter has been connected to the urinary drainage bag and it has been determined that there will be no pull on the catheter.

After preliminary cleansing of the skin at the holder site with an alcohol sponge (it is probably best to shave any hair at the site), the protective backing is stripped away from the adhesive side and the holder is placed on the thigh as described above. The umbilical tape is then tied in a bow-knot around the hard urinary drainage bag connector in such a manner that the holder and the connector are approximated. No other retaining or supporting devices such as safety pins are needed and the patient can move freely in bed or be ambulatory without discomfort.

This holder, although designed primarily for use with urethral catheters, can be utilized also for supporting nephrostomy tubes, cystostomy tubes, chest drainage tubes and other body cavity or organ drainage devices.

The outstanding value of this holder is primarily its simplicity, followed closely by patient comfort and patient acceptance.

DETAILED DESCRIPTION

Figure 1:
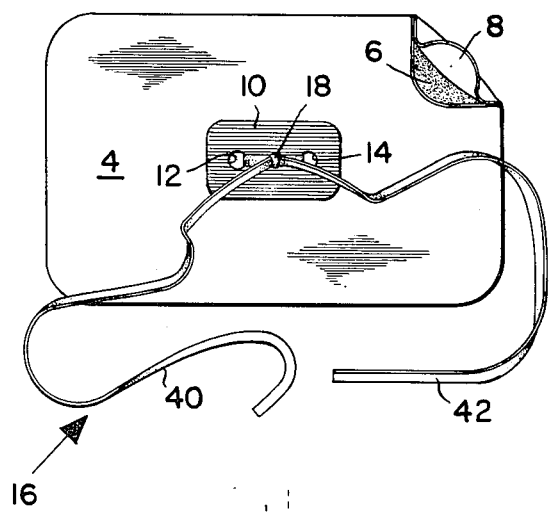
FIG. 1 is a top plan view of my catheter holder constructed in accordance with the invention.

A catheter holder 2 for securing a urethral catheter to a patient in accordance with the invention has a flexible anchoring strip 4 that is made of any suitable material, for example a woven fiber glass fabric. Strip 4 has its back face covered with a pressure-sensitive adhesive layer 6 (FIG. 1) that is covered in turn by a peel-off cover sheet 8. Pressure-sensitive adhesives for use against skin are well known, being widely used, for example, in connection with bandages. A flexible reinforcing panel 10 of, for example, a plastic such as cellophane or polyethylene overlies the center of strip 4. A pair of openings 12 and 14 through reinforcing panel 10 and strip 4 have a cord 16 looped therethrough and tied adjacent reinforcing panel 4 to form a knot 18. A flat cord such as umbilical tape is advantageous.

Figure 2:
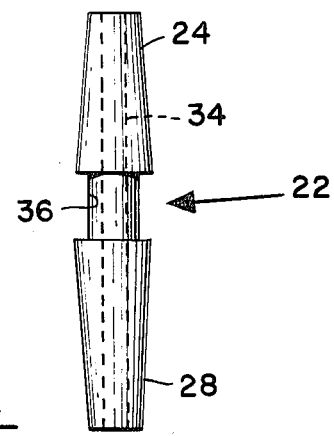
FIG. 2 is a plan view of a connector adapted to connect a catheter and drain tube, the connector is part of the drainage bag system.
Figure 3:
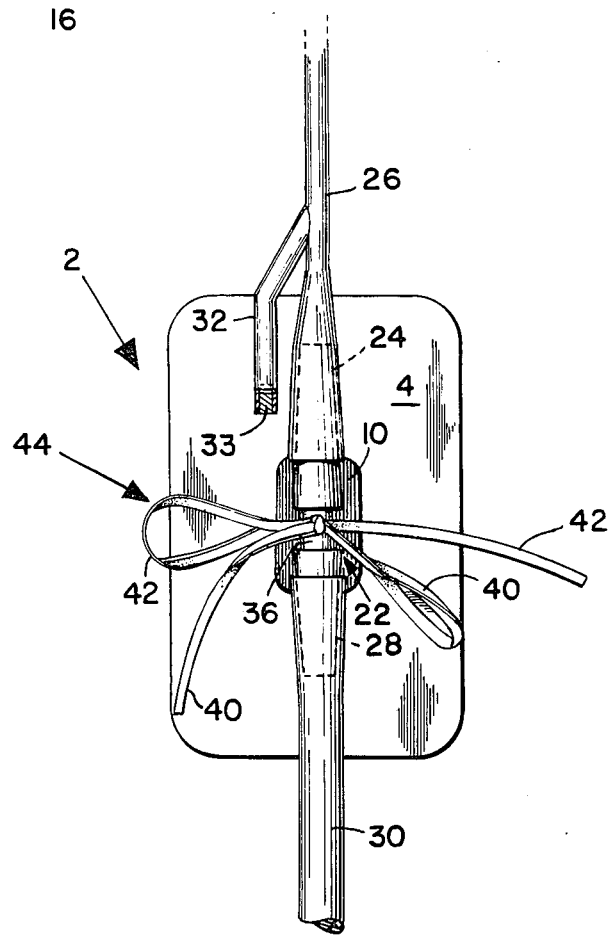
FIG. 3 is a plan view of a catheter holder of the invention attached to a urethral catheter and a drainage bag system.

An elongated connector 22 (FIG. 2) has a slightly tapered end 24 adapted to be telescoped into a urethral catheter 26 (FIG. 3) and a slightly tapered end 28 adapted to be telescoped into a drain tube 30. Urethral catheter 26 has a branch tube 32 containing a plug 33 through which a needle attached to a syringe may be passed for the purpose of introducing a fluid into catheter 26. A passage 34 (FIG. 2) in connector 22 provides for communication between urethral catheter 26 and drain tube 30. A peripheral groove 36 (FIG. 2) is formed in connector 22 intermediate its ends for the reception of cord 16.

Figure 4:
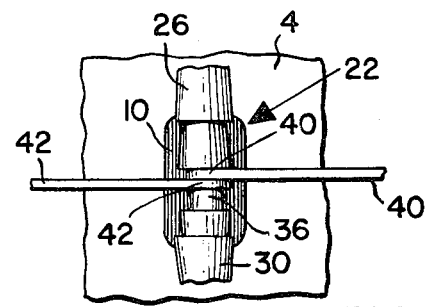
FIG. 4 is a view of the structure of FIG. 3, partially broken away, showing the cord after it has been looped around the connector and before it has been tied.
Figure 5:
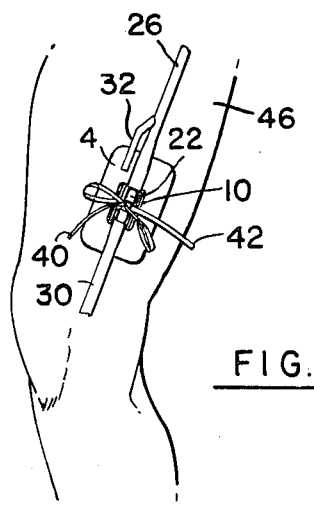
FIG. 5 is an elevational view showing the catheter holder of FIG. 3 secured to the right leg of a patient.

With the inner end (not shown) of the catheter 26 properly positioned in the patient, end 24 of fitting 22 is positioned in catheter 26, and the other end 28 of fitting 22 is positioned in drain tube 30. Cover sheet 8 is peeled off adhesive layer 6 and is then forced against, for example, the right thigh 46 of the patient (FIG. 5) adjacent the position it is desired to secure the connector 22. Portions 40 and 42 of cord 16 which are on opposite sides of knot 18 are now taken and looped around fitting 22 in opposite directions in groove 36 (FIG. 4) and then tied together in a bow-knot 44 (FIG. 3) to tie connector 22 against anchoring strip 4.

With cord 16 tightly tied in groove 36 the movement of catheter 26 is restricted to a distance less than the width of groove 36 which insures that the inner end of the catheter 26 remains in the desired position. Both the catheter 26 and drain tube 30 may be detached and attached to the connector 22 without disturbing the position of connector 22 on thigh 46. Similarly, connector 22, catheter 26 and tube 30 are readily removed by simply untying cord 16 from connector 22 without disturbing the attachment of securing strip 4 to thigh 46.

It will be understood that the above described embodiment is illustrative and is not intended to be limiting.

I claim:

1. A catheter holder for securing a urethral catheter to a patient comprising:
   a flexible anchoring strip having a pressure-sensitive adhesive layer on one side for securing the anchoring strip to a patient's skin,
   a cord secured to the anchoring strip with cord ends extending from the anchoring strip,
   said cord ends adapted to be looped around a peripheral groove in a connector between a catheter and a drain tube, and tied to secure the catheter holder to said groove,
   said anchoring strip having a pair of openings through which the cord passes and the cord is tied to secure to the anchoring strip,
   said anchoring strip having a reinforcing panel to reinforce the anchoring strip in the vicinity of the openings.

2. A catheter holder for securing a urethral catheter to a patient comprising:
   a flexible anchoring strip having a pressure-sensitive adhesive layer on one side for securing the anchoring strip to a patient's skin,
   a cord secured to the anchoring strip with cord ends extending from the anchoring strip,
   said cord ends adapted to be looped around a peripheral groove in a connector between a catheter and a drain tube, and tied to secure the catheter holder to said groove,
   a peel-off cover sheet covering the adhesive layer,
   the cord being a flat tape and passing through a pair of openings in the anchoring strip to which it is tied, and
   a reinforcing panel reinforcing the anchoring strip in the vicinity of the said openings.

* * * * *